(12) United States Patent
DiCarlo

(10) Patent No.: US 8,029,484 B2
(45) Date of Patent: Oct. 4, 2011

(54) UNIVERSAL DIAPER

(76) Inventor: Mary Margaret DiCarlo, Pittsburg, PA (US)

( * ) Notice: Subject to any disclaimer, the term of this patent is extended or adjusted under 35 U.S.C. 154(b) by 902 days.

(21) Appl. No.: 11/878,813

(22) Filed: Jul. 27, 2007

(65) Prior Publication Data

US 2009/0030388 A1    Jan. 29, 2009

(51) Int. Cl.
A61F 13/15 (2006.01)
(52) U.S. Cl. ....... 604/385.101; 604/385.11; 604/385.13; 604/385.22
(58) Field of Classification Search ............. 604/385.06, 604/385.13, 393–396, 402, 385.101, 385.11, 604/385.22
See application file for complete search history.

(56) References Cited

U.S. PATENT DOCUMENTS

| | | |
|---|---|---|
| 889,827 A | 6/1908 | Tenfel |
| 1,875,740 A | 9/1932 | Klein |
| 2,796,064 A * | 6/1957 | Green et al. .................. 604/394 |
| RE26,151 E | 1/1967 | Duncan |
| 3,369,545 A | 2/1968 | Wanberg |
| 3,585,998 A | 6/1971 | Hayford et al. |
| 3,613,686 A | 10/1971 | De Woskin |
| 3,838,692 A | 10/1974 | Levesque |
| 3,875,942 A | 4/1975 | Roberts et al. |
| 3,964,486 A | 6/1976 | Blaney |
| 4,019,517 A | 4/1977 | Glassman |
| 4,022,210 A | 5/1977 | Glassman |
| 4,085,753 A | 4/1978 | Gellert |
| 4,221,221 A | 9/1980 | Ehrlich |
| 4,352,356 A * | 10/1982 | Tong .............................. 604/402 |
| 4,430,087 A | 2/1984 | Azpiri |
| 4,493,713 A | 1/1985 | Izzo |
| 4,534,769 A * | 8/1985 | De Jonckheere et al. ..... 604/369 |
| 4,623,339 A | 11/1986 | Ciraldo |
| 4,685,909 A | 8/1987 | Berg et al. |
| 4,702,378 A | 10/1987 | Finkel et al. |
| 4,738,678 A | 4/1988 | Paulis |
| 4,743,240 A | 5/1988 | Powell |
| 4,753,643 A | 6/1988 | Kassai |
| 4,753,647 A | 6/1988 | Curtis |
| 4,790,836 A | 12/1988 | Brecher |
| 4,790,840 A | 12/1988 | Cortina |
| 4,808,175 A | 2/1989 | Hansen |
| 4,917,693 A | 4/1990 | Terry |
| 4,923,455 A | 5/1990 | Dean et al. |
| 4,931,052 A | 6/1990 | Feldman |
| 4,964,859 A | 10/1990 | Feldman |
| 4,968,311 A | 11/1990 | Chickering et al. |
| 5,141,505 A | 8/1992 | Barrett |
| 5,207,663 A | 5/1993 | McQueen |

(Continued)

*Primary Examiner* — Lynne Anderson
(74) *Attorney, Agent, or Firm* — Barley Snyder LLC (57) ABSTRACT

A two-way stretch disposable diaper formed from four cooperating layers, a microfiber top layer to keep the wearer dry, an absorbent pad to collect body exudates, a waterproof layer to keep absorbed fluids within the pad, and a two-way stretch outer support layer. The top layer is formed as a cover for the absorbent pad which is designed to absorb urine and semi-liquid fecal material. The absorbent pad is backed by the waterproof layer or sheet which also covers the pad edges to prevent side leakage. The waterproof layer is anchored to a self-adhesive, two-way stretch support layer which constitutes an outer cover or support layer. The support layer derives its two way stretch and self adhesive qualities from its weave of alternate twist and/or crinkle threads. The support layer includes a plurality of holes in the waist band area which provide added ventilation and drainage when the diaper is used as swim-wear.

23 Claims, 9 Drawing Sheets

U.S. PATENT DOCUMENTS

| | | | |
|---|---|---|---|
| 5,304,158 A | 4/1994 | Web | |
| 5,429,628 A | 7/1995 | Trinh et al. | |
| 5,443,161 A | 8/1995 | Jonese | |
| 5,582,605 A | 12/1996 | Lepie | |
| 5,689,836 A * | 11/1997 | Fee et al. | 2/465 |
| 5,733,272 A | 3/1998 | Brunner et al. | |
| 5,769,832 A | 6/1998 | Hasse | |
| 5,769,833 A | 6/1998 | Hasse | |
| 5,778,110 A | 7/1998 | Furuya | |
| 5,989,236 A | 11/1999 | Roe | |
| 6,004,307 A | 12/1999 | Colon et al. | |
| 6,107,537 A | 8/2000 | Elder et al. | |
| 6,160,198 A | 12/2000 | Roe et al. | |
| 6,262,331 B1 | 7/2001 | Nakahata et al. | |
| 6,306,782 B1 | 10/2001 | Tsai | |
| 6,369,290 B1 | 4/2002 | Glaug et al. | |
| 6,384,296 B1 | 5/2002 | Roe et al. | |
| 6,454,748 B1 | 9/2002 | Ives | |
| 6,475,204 B1 | 11/2002 | Walker | |
| 6,476,288 B1 | 11/2002 | VanRijswijck et al. | |
| 6,497,694 B1 | 12/2002 | Rosch et al. | |
| 6,596,920 B2 | 7/2003 | Wehner et al. | |
| 6,610,381 B1 | 8/2003 | Conway | |
| 6,627,788 B1 | 9/2003 | Kuen | |
| 6,703,536 B2 | 3/2004 | Roe et al. | |
| 6,712,801 B1 | 3/2004 | Richardson | |
| 6,723,080 B1 | 4/2004 | Habib et al. | |
| 6,733,484 B2 * | 5/2004 | Van Gompel et al. | 604/385.16 |
| 6,756,522 B2 | 6/2004 | Sayama et al. | |
| 6,803,496 B2 | 10/2004 | Elder et al. | |
| 6,822,136 B1 | 11/2004 | Niemeyer et al. | |
| 6,863,665 B2 | 3/2005 | Rosch et al. | |
| 6,994,761 B2 | 2/2006 | Klemp et al. | |
| 7,104,977 B2 | 9/2006 | Price | |
| 7,105,715 B2 | 9/2006 | Carlucci et al. | |
| 7,198,621 B2 | 4/2007 | Moser | |
| 7,204,907 B2 | 4/2007 | Cree | |
| 2004/0092901 A1 * | 5/2004 | Reece et al. | 604/385.06 |
| 2005/0020347 A1 | 1/2005 | Moshal | |
| 2005/0177120 A1 | 8/2005 | Olson | |
| 2005/0256487 A1 | 11/2005 | Williams | |
| 2006/0052761 A1 | 3/2006 | Snell | |
| 2006/0282053 A1 * | 12/2006 | Rohrl | 604/385.01 |
| 2007/0142812 A1 | 6/2007 | Popp et al. | |

* cited by examiner

UNIVERSAL DIAPER

FIELD OF THE INVENTION

The present invention relates to a breathable, medicated, universal diaper adaptable for a wide range of body types and sizes which may be used as a standard diaper or a swim wear diaper combined with a pouch containing personal care products and which may be used for disposal of the diaper after use.

BACKGROUND OF THE INVENTION

Infants and other incontinent individuals wear absorbent articles such as diapers and incontinent briefs to receive and contain discharged urine and other body exudates. Such absorbent articles function both to contain the discharged materials and to isolate those materials from the body of the wearer and from the wearer's garments and bed clothing. Disposable absorbent articles having many different basic designs are known in the art. For example, Duncan et al., U.S. Reissue Pat. No. Re. 26,152, for "Disposable Diaper," issued Jan. 31, 1967, describes a basic disposable diaper structure that has achieved wide acceptance and considerable commercial success.

DISCUSSION OF THE RELATED ART

A review of the prior art related to disposable diapers has indicated a need for a two-way stretch garment to comfortably accommodate all body types and sizes and provide ventilation around the wearer's back and stomach to prevent heat rash. Also needed is a disposable diaper that can serve as an absorbent swim-wear garment that provides urine and bowel movement containment before and during swimming and allow drainage of excess water from the garment after swimming without undesirable discharge of bodily waists.

Numerous attempts have been made to create absorbent articles with multiple stretch direction properties. A typical example is the U.S. Patent Application Publication No. 2007/0142812 by Popp, et al. for "Absorbent Garments with Multipart Liner Having Varied Stretch Properties" which has three stretch zones. A first edge zone and a second edge zone are separated by a middle zone which has different stretch-direction characteristics than the edge zones. Production of such garments is labor intensive and their marketing requires a large inventory of different sizes for a variety of different body types.

Attempts have been made to provide ventilation, but the vents are not positioned in the needed areas. A typical example is U.S. Pat. No. 6,994,761 issued to Klemp, et al., for "Disposable Absorbent Garment such as a Diaper or Training Pants and a Process of Making the Same". In such garments the vents are positioned along the sides to avoid leakage and by being so placed, they fail to provide ventilation in the areas most in need.

D. Kuen, U.S. Pat. No. 6,627,788 for "Swimwear with Water Drains", Sep. 30, 2003, is an example of currently available, absorbent, swimwear garments having a water drain in the crotch area. A drain opening in this area allows urine and water soluble material to drain with the water accumulated inside the diaper and prevents air circulation around the wearer's waist.

Y. Nakahata, et al., U.S. Pat. No. 6,262,331 for "Absorbent Article Having a Topsheet that Included Selectively Openable and Closable Openings", issued Jul. 17, 2001, incorporates a plurality of openings in the back panel of a diaper but the openings are in the top sheet only so they do not provide a drain means or ventilation.

Disposable absorbent articles that include a top sheet having a single, relatively large area aperture to permit fecal material to pass there through are known. Such structures are directed to isolating the fecal material from the body of the wearer. Examples of such known structures are disclosed in Allen et al., U.S. Pat. No. 5,037,416, for "Disposable Absorbent Article Having Elastically Extensible Topsheet," issued Aug. 6, 1991; Freeland et al., U.S. Pat. No. 5,269,775, for "Trisection Topsheets for Disposable Absorbent Articles and Disposable Absorbent Articles Having Such Trisection Topsheets," issued Dec. 14, 1993; and U.S. Pat. No. 5,624,422, for "Absorbent Article Having an Extendible Split Core," issued Apr. 29, 1997, to Allen. All such diapers are available in a variety of standard sizes that do not fit comfortably for many body types or sizes.

OBJECTIVES OF THE INVENTION

The underlying objective of the invention is to provide a universal diaper adaptable for a wide range of body types and sizes by virtue of its elastic properties which are obtained via weaving techniques and without the use of elastic composition threads.

A significant objective is the production of a disposable garment manufactured in a single size adaptable for use by persons of a wide range of body types and sizes to thereby minimize retail inventory and maximize profits.

Another objective is to provide a diaper which will absorb and isolate urine and fluid fecal material from the body of the wearer.

A further objective is to provide a disposable diaper that will adapt to any body size and type by being fabricated from fabric woven to permit two-way stretch.

A still further objective is to provide a disposable diaper that is comprised of a layered assembly wherein the outer support layer is self-adhesive.

Another objective is to provide a diaper with an outer support layer woven from yarns selected from the class of yarns fabricated from the class of threads including crinkle threads and alternately twisted threads to provide a two-way stretch fabric.

Another objective is to provide a disposable diaper with a self contained, odor and moisture proof soiled diaper disposal containment means.

Another objective is to provide a disposable diaper with a moisture activated deodorant calculated to mask the odor of urine and feces.

A further objective is to provide a disposable diaper with an outer support layer fabricated from a material that has a self-sticking property so pins, tape, adhesive, or other securing means are not needed.

Another objective is to provide a disposable diaper with a self contained pouch for storing personal hygiene items and after the diaper has been used, serve as an odor and moisture proof soiled diaper disposal containment means.

A further objective of the present invention to provide a disposable absorbent article that is so configured as to provide an odor masking enclosure means which will function as a container to hold the soiled, urine soaked diaper pad and semi-solid and fluid fecal material that is received in the diaper during use. Additionally, the containment means functions to provide a means to store personal hygiene items such as lotions, deodorants, and so forth to be used on the wearer prior and/or after use of the diaper.

The foregoing and other objectives will become apparent in light of the following specification and drawings which present the best reduction to practice known to the inventor at this time.

SUMMARY OF THE INVENTION

The present invention comprises a disposable diaper incorporating a microfiber top layer to keep the wearer dry. The top layer is formed as a cover for an absorbent pad designed to absorb urine and semi-liquid fecal material. The absorbent pad is backed by a waterproof layer or sheet which also covers the pad edges to prevent side leakage. The waterproof layer is anchored to a self-adhesive, two-way stretch support layer which constitutes an outer cover or backing sheet. The Support layer derives its two way stretch and self adhesive qualities from its weave of alternate twist and/or crinkle threads. The support layer includes a plurality of holes in the waist band area which provide added ventilation and drainage when the diaper is used as swim-wear.

The disposable diaper is provided as a kit which includes a pouch secured to the outside of the outer support layer of the disposable diaper. The pouch may contain a waterproof, odor-proof, sealable, sanitary bag for containing the diaper for disposal, or the pouch may be waterproof and serve as a sealable, odor-proof diaper disposal container. The preferred pouch content, according to this invention, is a disposable changing cloth, a sanitizing wipe, a packet of diaper rash cream and a deodorant. The disposable diaper kit also includes an anti-diaper rash compound in the form of a medicated cream or ointment pre-applied to the crotch area.

DESCRIPTION OF THE PREFERRED EMBODIMENT

Figure 1:
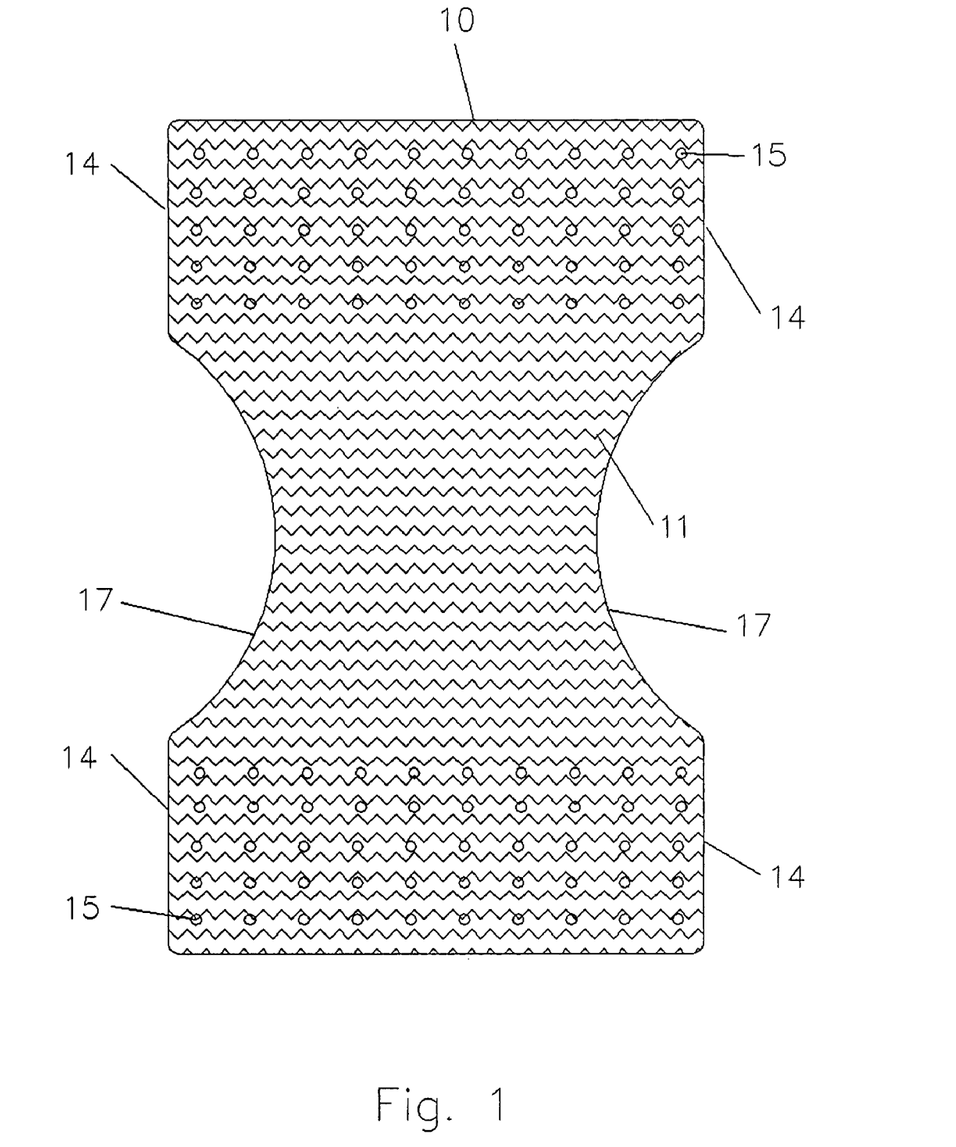
FIG. 1 is a plan view as taken from the body side or inside, of the diaper outer support layer illustrating the warp thread directions used in the material weave arranged to provide stretch in girth.

The invention is a disposable diaper and ancillary pouch. The diaper per se has a semi hourglass shape to accommodate the wearer's thighs and is comprised of three layers, an outer stretch layer, a waterproof layer and an inner absorbent layer. The outer layer is illustrated by FIG. 1. it is fabricated from a crinkle weave stretch material, 10, similar to that described in U.S. Pat. No. 3,221,736 to Heitzmann for "Dressings and Bandages". As an alternative, the stretch material may be a woven fabric created according to Klein, U.S. Pat. No. 1,875, 740 and/or Teufel, U.S. Pat. No. 889,827. for "Elastic Woven Bandage" wherein the warp threads are tightly twisted in a repeating pattern with every other thread having a left hand twist and the intermediate threads a right hand twist. (The teachings of the foregoing patents are incorporated herein by reference.) This last weaving technique is referred to herein as the Teufel weave. The material has a self-sticking property so pins, tape, adhesive, or other securing means are not needed. The wings, 11, are simply overlapped and pressed together while a slight tension is maintained to stretch the material enough to cause self adhesion. A plurality of holes, 12, are provided in the waist band area to enhance breathing of the material and speed draining when the diaper is used for swimming. The holes are shown as being located in the back and belly-band area but they can be restricted to the back or other areas or cover the complete diaper.

Figure 2:
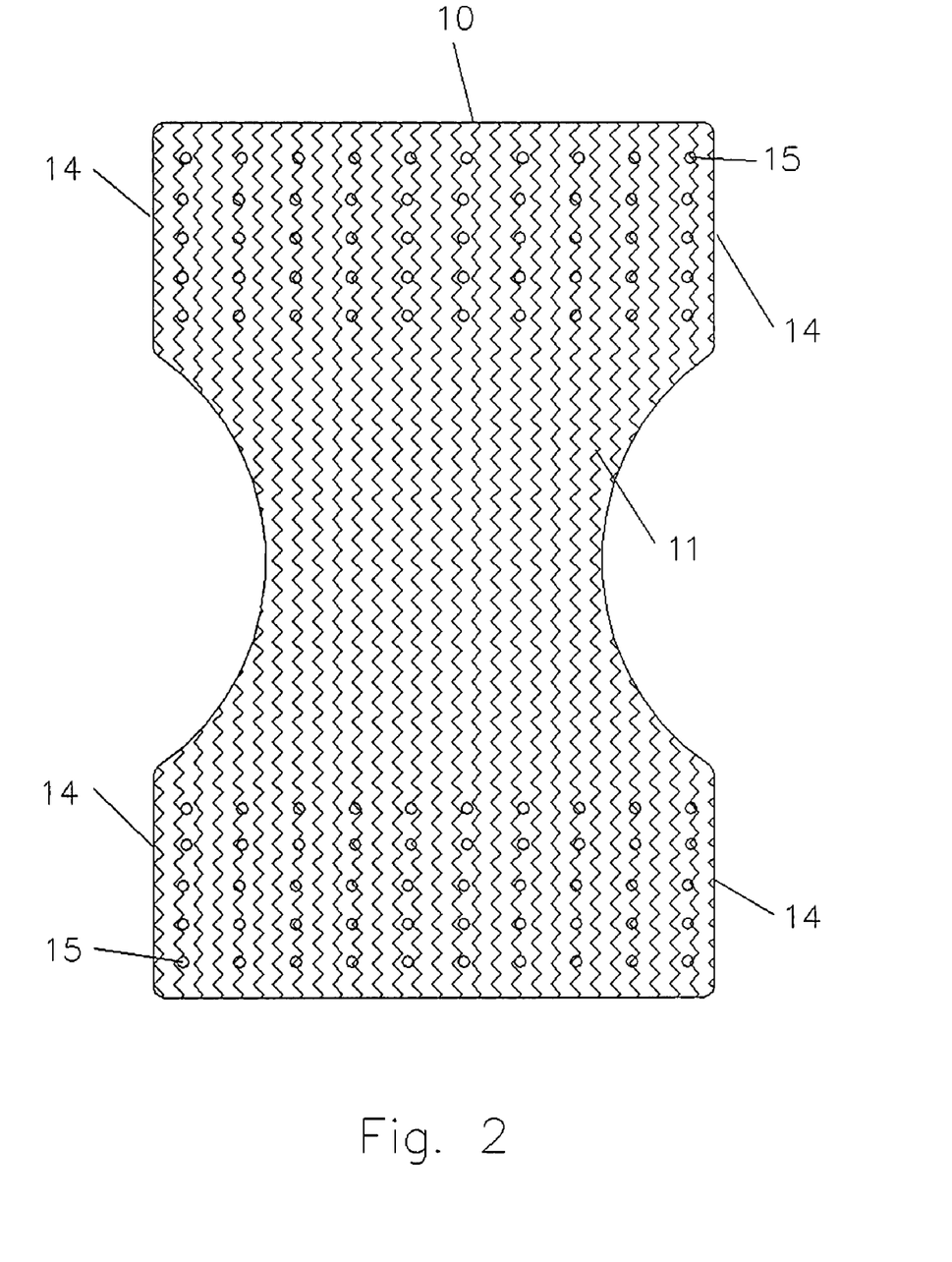
FIG. 2 is a view of the diaper outer support layer illustrating the warp thread directions used in the material weave arranged to provide stretch in length.

The orientation of the weave of the material used to fabricate the outer layer controls the direction of stretch. When the crinkle yarn 11 runs from side to side as illustrated by FIG. 1, maximum stretch is provided in girth to accommodate persons of a wide range of weights. When the crinkle yarn used as threads runs from front to back as illustrated by FIG. 2, maximum stretch is provided from top to bottom to accommodate persons of different heights. An elastic material may be used as edging 17 to prevent leakage of any material that escapes the absorbent pad assembly.

Figure 3:
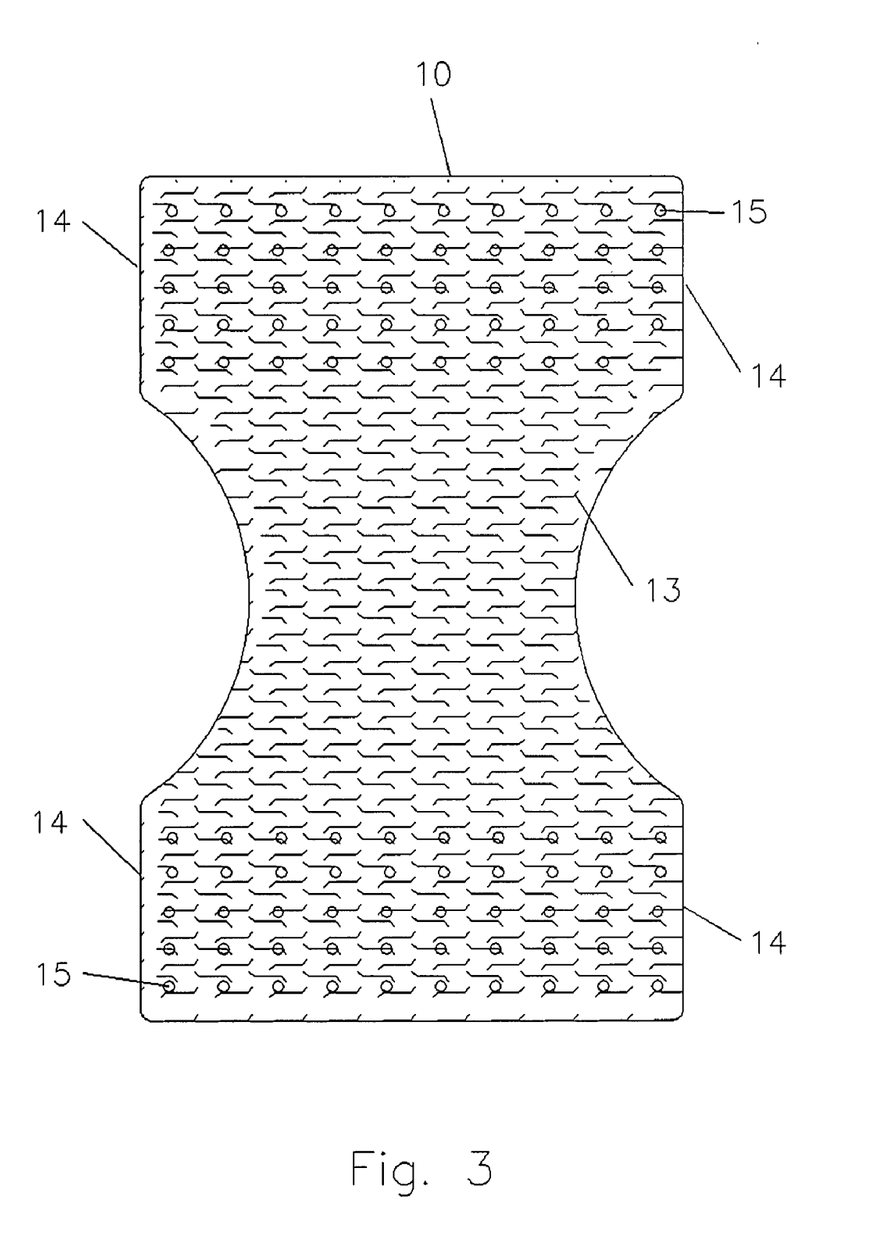
FIG. 3 is a view of the diaper outer support layer illustrating the warp thread directions used in the material weave arranged to provide stretch in girth as a function of the warp thread twist technique.

If the Teufel weave technique is used, stretch direction is controlled by the direction of the threads 13 just as when crinkled yarn techniques are used as in FIGS. 1 and 2. FIG. 3 is an example of a Teufel type weave with the warp running from side to side to accommodate different widths or girths, as in FIG. 1.

Figure 4:
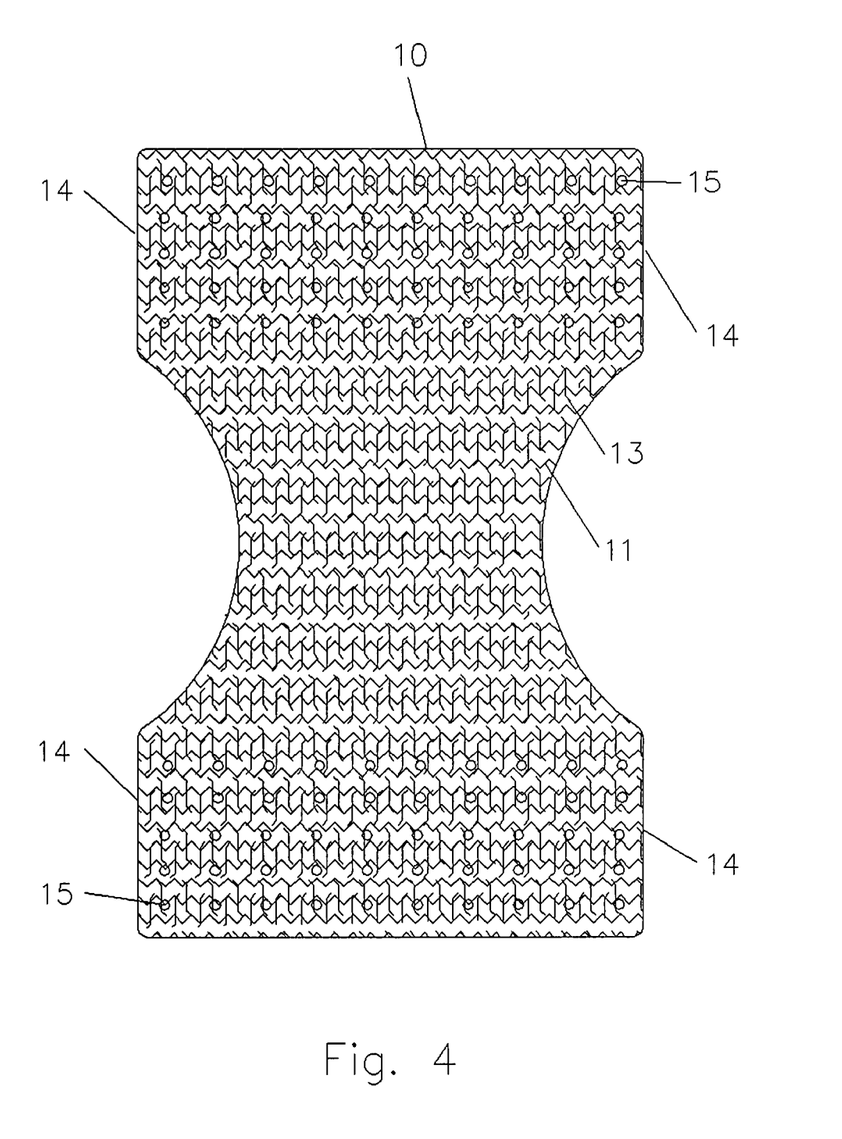
FIG. 4 is a view of the diaper outer support layer illustrating the warp thread directions used in the material weave arranged to provide stretch in length wherein the weft threads comprise crinkle threads to provide stretch in girth.

The foregoing embodiments do not satisfactorily accommodate all body types. However, this is accomplished by the preferred embodiment which combines crinkle yarn with a Klein or Teufel type weave. FIG. 4 illustrates one of the possible combinations where crinkled threads are used for weft threads 11 in a Klein or Teufel type weave where the twisted threads 13 are the warp threads. In FIG. 4, the twisted Klein or Teufel threads 13 providing stretch from top to bottom and the crinkle threads 11 used as weft threads provide the stretch in girth. This embodiment has the added benefit derived from the fact the self adhesive properties are strongest in the girth direction which allows for a firmer adhesion of the wings 14 when the diaper is worn.

Figure 5:
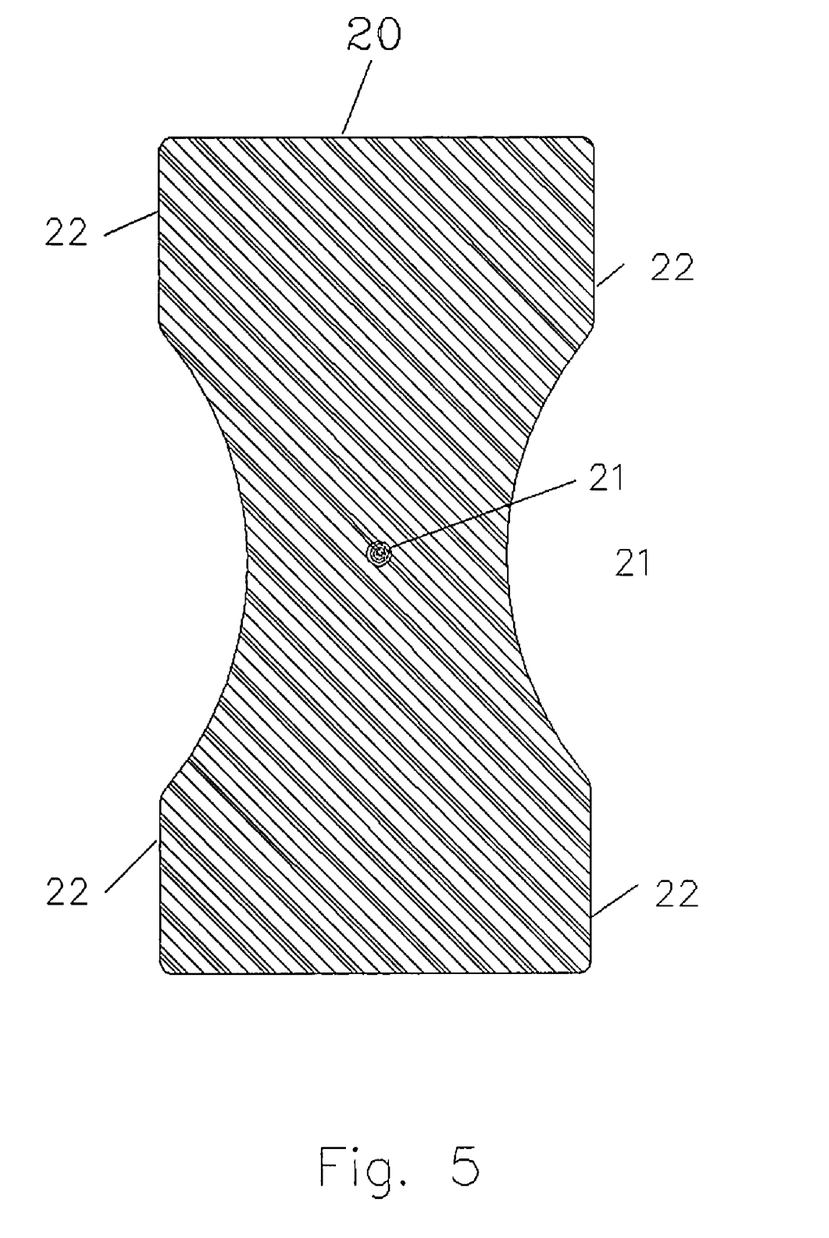
FIG. 5 is a plan view of the water-proof film secured to the inside of the outer layer.

FIG. 5 depicts the waterproof plastic film which forms the next layer. It is firmly secured at its center, 21, to the outer layer by an adhesive or other means such as sewing, etc. A securing means is employed to firmly hold the center the plastic film to the center of the outer layer without impeding the stretch properties of the outer, support layer. Additional means are employed to hold the plastic film, 20, in position while it is being donned. This is accomplished by lightly securing the film to the outer layer at a number of strategic points, 22, with a weak adhesive calculated to avoid impeding the stretch of the outer layer by breaking free under a slight shearing force. The lightly secured points 22 hold the film properly positioned on the outer layer while it is being secured about a wearer but break free once the diaper outer layer is stretched to accommodate the size and body type of the wearer. The plastic sheet prevents leakage from the absorbent pad 30 of FIG. 6 and through the outer layer.

Figure 6:
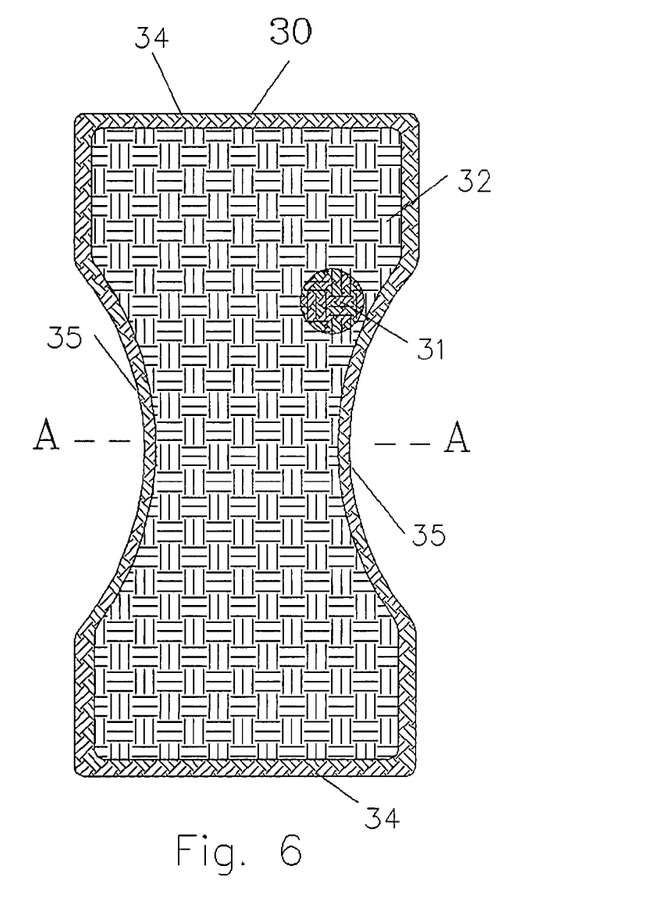
FIG. 6 is a plan view of the adsorbent pad inner layer.

The adsorbent pad inner layer 30, illustrated by FIG. 6, is comprised of an absorbent layer 31 covered by a non-absorbent, porous top sheet 32 which permits the passage of urine and semi-liquid feces while keeping the wearer's skin separated from the absorbent layer and thereby dry. In a preferred embodiment the porous top sheet is fabricated from a micro fiber material with an acetic moisture activated deodorant calculated to mask the odor of urine and feces. The deodorant is in the form of a coating which remains on the inside of the micro-fiber material to prevent it from contacting the wearer's skin. In the preferred embodiment, the material is an odor suppressant which migrates into the pad when wetted. It is selected from a group of compounds which are activated by a weak acid solution.

Figure 7:
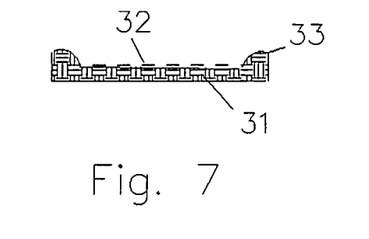
FIG. 7 is a cross sectional view of the pad illustrated in FIG. 6 taken along the line A-A.

The absorbent pad subassembly of the diaper has a thickening edge, 33, to keep solids and odors within the pad area. The thick edge and layers comprising the absorbent pad inner layer 30 are more clearly illustrated in the cross sectional view of FIG. 7. The thickness of the thickening edge may be thinner at the ends of the pad, 34, than at the sides, 35, to provide a more comfortable fit for reclining wearers. It may be secured to the plastic film layer by any flexible, waterproof means, such as an adhesive but in the preferred embodiment of FIG. 8, the plastic sheet 20 is wrapped around the pad edges 33, and this creates a secure subassembly.

Figure 8:
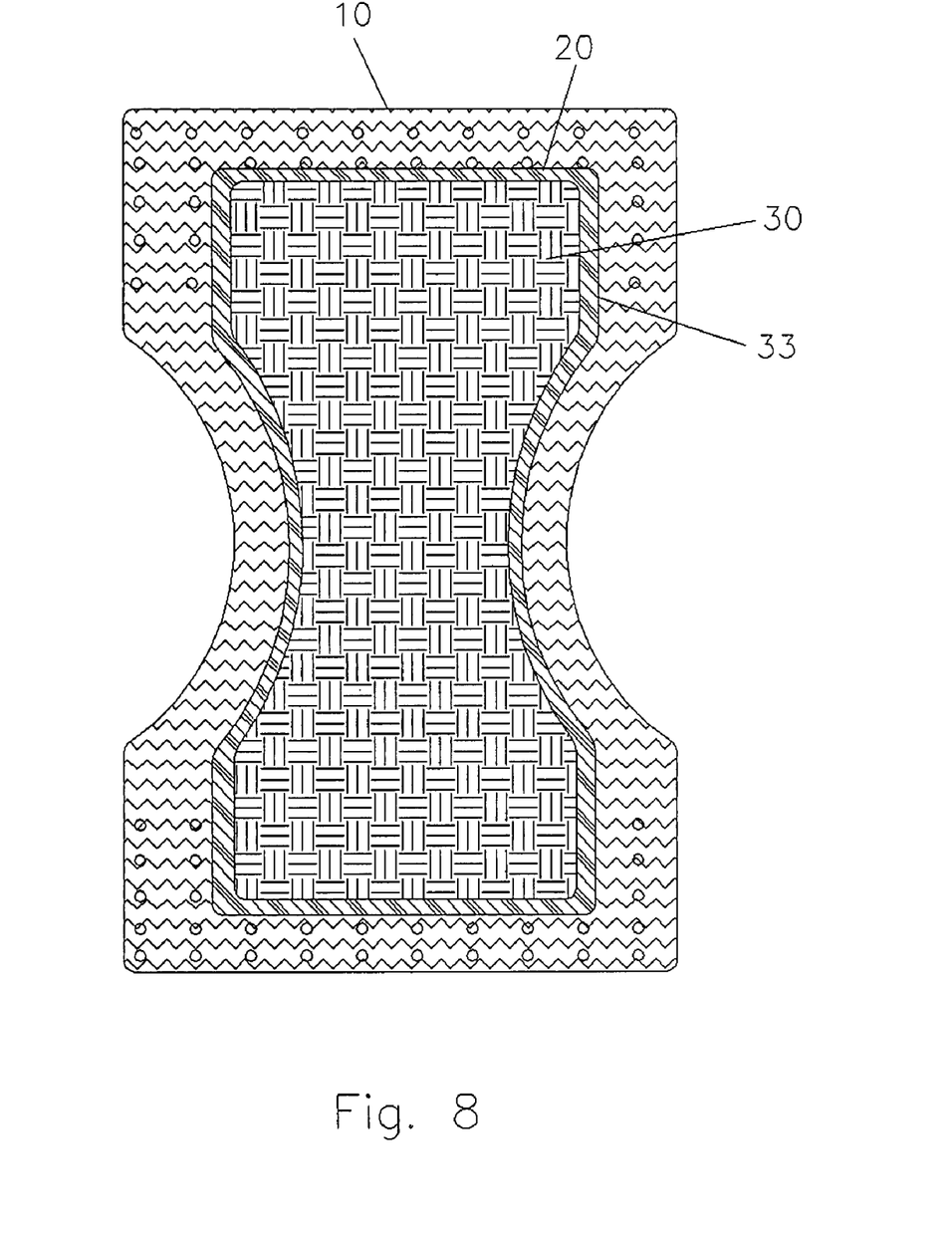
FIG. 8 is the assembled diaper as viewed from the inside. Note that the edges of the plastic film layer are wrapped over the thickening edge of the pad.

FIG. 8 is the assembled diaper as seen from the inside, i.e., wearer or skin side. Note that the edges of the plastic film layer 20 are wrapped around the thickening edge 33 of the pad 30. This prevents leakage between the wearer's skin and the pad because the resiliency of the outer support layer gently holds the sealing bead against the wearer's skin. After use, the diaper may be rolled or folded so that the plastic film layer contains all of the waste and absorbent pad and the self adhesive qualities of the outer layer will secure the package.

Figure 9:
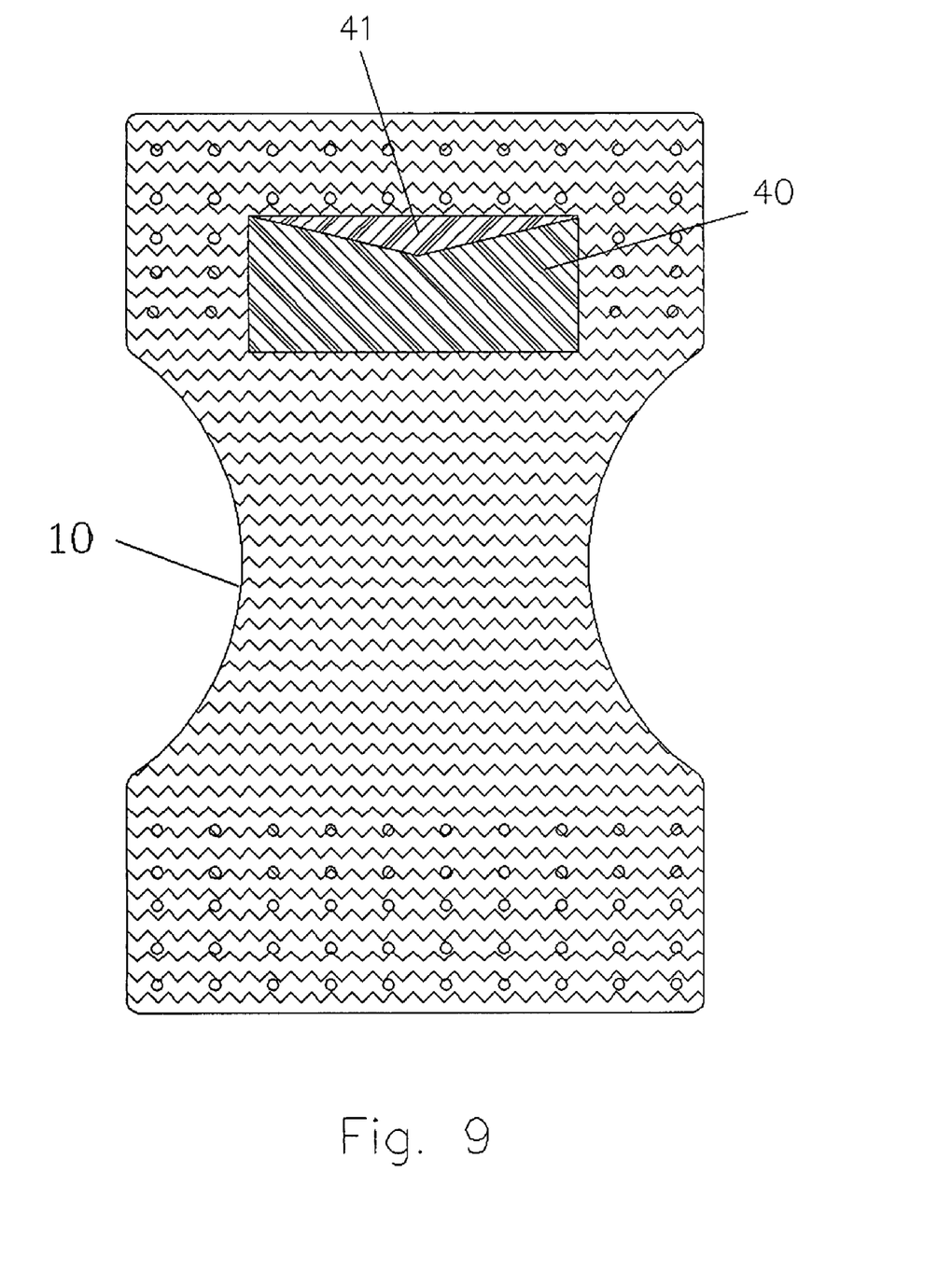
FIG. 9 is an exterior view of the assembled diaper illustrating the pouch which may contain various hygienic aids and serve as a disposal container.

FIG. 9 is an exterior view of the assembled diaper illustrating an optional pouch 40 which may contain various hygienic aids and serve as a disposal container. The pouch is secured to the outer layer along its top edge only so the diaper, when soiled, may be rolled and/or folded into it. This action covers the flap closer 41 shown in the figure but a second flap, not shown, inside the pouch along the front edge may be folded out to secure the package. The pouch is fabricated from a waterproof material and has a pleated side and bottom configuration so that it may be expanded to hold the soiled diaper or other items.

Figure 10:
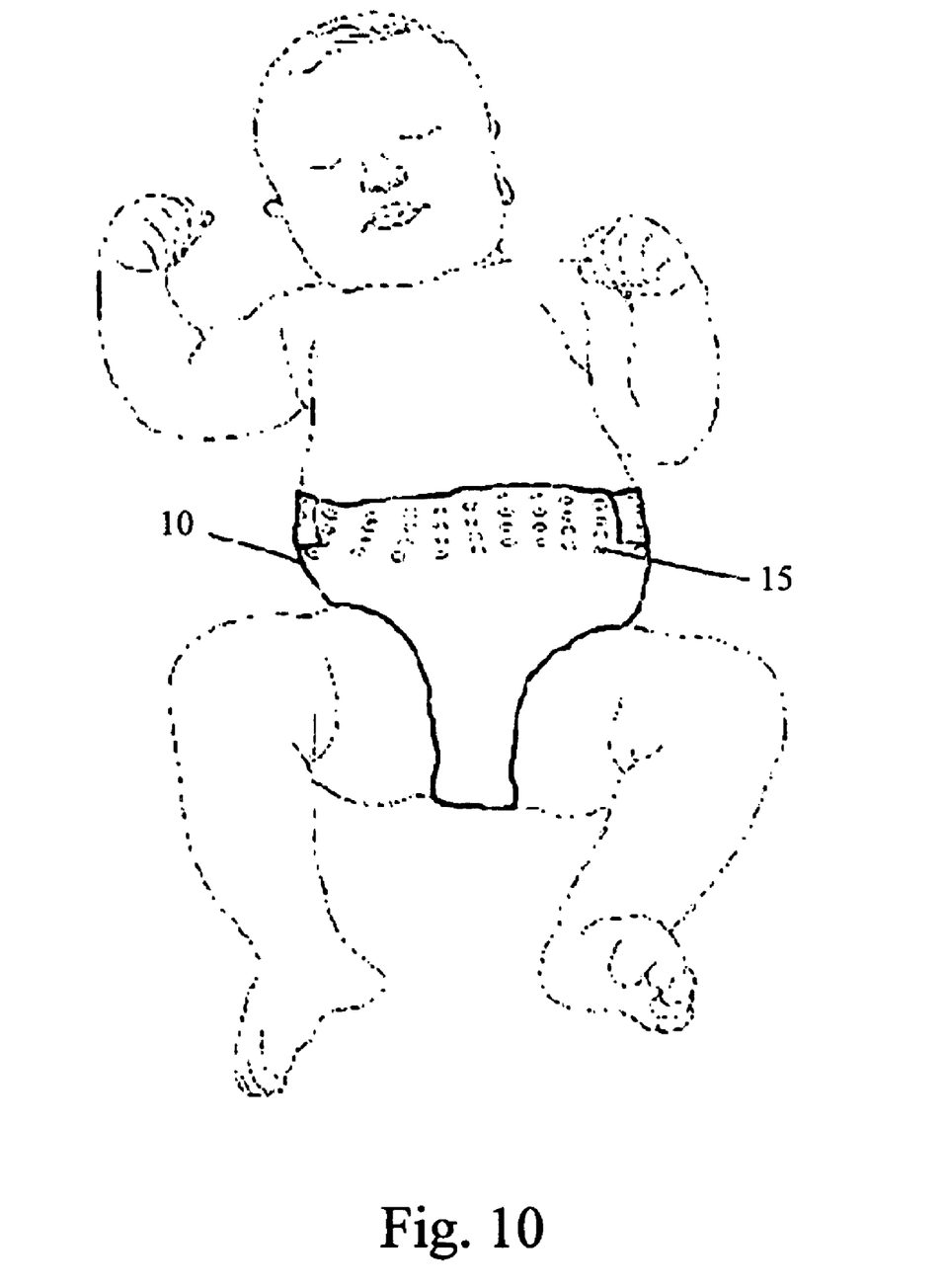
FIG. 10 illustrates the diaper as it is worn.

The preferred embodiment of the invention is illustrated in FIG. 10 which demonstrates the adaptability of the novel diaper 10 disclosed herein fabricated with an outer support layer, comprised of a self-adhesive fabric stretchable in two dimensions. This is achieved as previously explained by using a cloth woven from yarns selected from the class of yarns fabricated from the class of threads including crinkle threads and alternately twisted threads. That is, in the preferred embodiment, crinkled threads are used for weft threads in a weave having alternately twisted warp threads. In FIG. 10, note that the rotund baby stretches the girth of the diaper as indicated by the elongation of the vent holes and the large torso stretches the crotch in a length-wise direction. In the preferred embodiment of FIG. 10, the outer support layer cloth is orientated so crinkle weft threads run from side to side and twisted warp threads run from top to bottom.

While preferred embodiments of this invention have been illustrated and described, variations and modifications may be apparent to those skilled in the art. Therefore, I do not wish to be limited thereto and ask that the scope and breadth of this invention be determined from the claims which follow rather than the above description.

What is claimed is:

1. A disposable absorbent garment, comprising:
an outer support layer prepared from a two-way stretch material;
a waterproof layer having a firmly fixed securing point positioned at a proximate center of the outer support layer that is spatially limited to a positioned midway between all edging of the waterproof layer, the firmly fixed securing point positioned to allow unimpeded stretch of the outer support layer;
an absorbent pad having an absorbent layer and a nonabsorbent porous top layer; and
the two-way stretch material holding garment adjacent to a lower torso of a wearer;
wherein the waterproof layer is further secured to the outer support layer by at least one lightly secured point positioned along side edges of the waterproof layer, the at least one lightly secured point connecting the waterproof layer and outer support layer and adapted to avoid impeding the stretch of the outer support layer by breaking free under a slight shearing force, the waterproof layer being less secure to the two-way stretch layer along the at least one lightly secured point than at the center.

2. The disposable absorbent garment according to claim 1, wherein the two-way stretch material comprises a woven material fabricated from a combination of yarns having twisted threads being warp threads twisted in alternate directions and accommodating differing heights of a user.

3. The disposable absorbent garment according to claim 2, wherein the woven material further comprises crinkle threads twisted in alternate directions, the crinkle threads used as weft threads providing stretch for differing girth of the user.

4. The disposable absorbent garment according to claim 1, wherein the waterproof layer is positioned on the outer layer while the disposable absorbent garment is being secured about a user, the at least one lightly secured point breaks free once the outer support layer is stretched to accommodate the size and body type of the user.

5. The disposable absorbent garment according to claim 3, wherein the outer support layer, the waterproof layer and absorbent pad are configured to have an hourglass shape.

6. The disposable absorbent garment according to claim 1, wherein the waterproof layer is positioned between the absorbent pad and the outer support layer, the nonabsorbent porous top layer covering the absorbent pad.

7. The disposable absorbent garment according claim 6, wherein the absorbent pad includes edges thicker than a main section of the pad and the waterproof layer is wrapped around the thicker edges of the absorbent pad.

8. The disposable absorbent garment according to claim 1, further comprising a plurality of holes positioned in the outer support layer.

9. The disposable absorbent garment according to claim 1, wherein the plurality of holes are positioned along an entire surface of the outer support layer.

10. The disposable absorbent garment according to claim 1, further comprising a waterproof pouch positioned on the outside of the outer support layer along a top edge.

11. The disposable absorbent garment according to claim 10, wherein the waterproof pouch has a pleated side and bottom configuration and is dimensioned to receive and seal therein the absorbent garment after it has been soiled.

12. A disposable diaper, comprising:
a two-way stretch outer support layer;

a waterproof layer adjacent to one side of the two-way stretch outer support layer;

an absorbent pad positioned on the side of the waterproof layer opposite the two-way stretch outer support layer;

a nonabsorbent porous top layer secured over said absorbent pad;

a securing member firmly attaching the waterproof layer to a proximate center of the outer support layer with respect to all edging of the outer support layer to allow unimpeded stretch of the outer support layer; and at least one lightly secured point positioned along side edges of the waterproof layer, the at least one lightly secured point connecting the waterproof layer and outer support layer by a weak securing member adapted to avoid impeding the stretch of the outer support layer by breaking free under a slight shearing force, the waterproof layer being less secure to the two-way stretch layer along the at least one lightly secured point than at the center.

13. The disposable absorbent garment according to claim 12, wherein the waterproof layer is positioned on the outer layer while the disposable absorbent garment is being secured about a user, the at least one lightly secured point breaks free once the outer support layer is stretched to accommodate the size and body type of the user.

14. The disposable diaper according to claim 13, wherein the two-way stretch outer support layer comprises a woven material fabricated from a combination of yarns having crinkle threads twisted in alternate directions, the crinkle threads being weft threads providing stretch for differing girth of the user.

15. The disposable absorbent garment according to claim 14, wherein the two-way stretch outer support layer comprises further comprises warp threads twisted in alternate directions and accommodating differing heights of a user.

16. The disposable absorbent garment according to claim 14, wherein the outer support layer, the waterproof layer and absorbent pad are configured to have an hourglass shape.

17. The disposable absorbent garment according to claim 12, wherein the waterproof layer is positioned between the absorbent pad and the outer support layer, the nonabsorbent porous top layer covering the absorbent pad.

18. The disposable absorbent garment according claim 17, wherein the absorbent pad includes edges thicker than a main section of the pad and the waterproof layer is wrapped around the thicker edges of the absorbent pad.

19. The disposable absorbent garment according to claim 12, further comprising a plurality of holes positioned in the outer support layer.

20. The disposable absorbent garment according to claim 19, wherein the plurality of holes are positioned along an entire surface of the outer support layer.

21. The disposable absorbent garment according to claim 12, further comprising a waterproof pouch positioned on the outside of the outer support layer along a top edge.

22. The disposable absorbent garment according to claim 21, wherein the waterproof pouch has a pleated side and bottom configuration and is dimensioned to receive and seal therein the absorbent garment after it has been soiled.

23. A disposable absorbent garment, comprising:

an outer support layer configured with an hourglass shape with wide ends forming the front top and back of the garment when it is worn and functioning as securing device;

a waterproof layer having a firmly fixed securing point positioned at a proximate center of the outer support layer with respect to all edging of the waterproof layer to allow unimpeded stretch of the outer support layer;

an absorbent pad having an absorbent layer and a nonabsorbent porous top layer, the absorbent pad includes thickening edges that are thicker on the sides than on the top front and back;

a two-way stretch material holding garment adjacent to a lower torso of a wearer, the outer support layer prepared from the two-way stretch material, the two-way stretch material comprising a woven material fabricated from a combination of yarns having threads twisted in alternate directions and forming the woven materials of warp threads and yarns comprised of crinkle threads functioning as the woven materials weft threads;

drainage holes in the top front and back sections of said two-way stretch material;

an elastic edging along the sides of said two-way stretch material; and a waterproof pouch formed on and as part of the outer support layer and dimensioned to receive and seal therein the garment after it has been soiled.

* * * * *